(12) United States Patent
Coleman et al.

(10) Patent No.: US 7,757,572 B2
(45) Date of Patent: Jul. 20, 2010

(54) PRESSURIZED GAS SAMPLING CONTAINER

(76) Inventors: Todd Coleman, 13621 N. 200 East Rd., Fairmount, IL (US) 61841; Dennis Coleman, 2612 Nottingham Ct. S., Champaign, IL (US) 61821

( * ) Notice: Subject to any disclaimer, the term of this patent is extended or adjusted under 35 U.S.C. 154(b) by 0 days.

(21) Appl. No.: 10/578,973

(22) PCT Filed: Nov. 12, 2004

(86) PCT No.: PCT/US2004/038636

§ 371 (c)(1),
(2), (4) Date: May 11, 2006

(87) PCT Pub. No.: WO2005/047865

PCT Pub. Date: May 26, 2005

(65) Prior Publication Data
US 2007/0056394 A1    Mar. 15, 2007

Related U.S. Application Data

(60) Provisional application No. 60/519,410, filed on Nov. 12, 2003.

(51) Int. Cl.
*G01N 1/22* (2006.01)
(52) U.S. Cl. .................. 73/864.63; 73/864.65
(58) Field of Classification Search .............. 73/863.17, 73/863.86, 864.63
See application file for complete search history.

(56) References Cited

U.S. PATENT DOCUMENTS

| | | | |
|---|---|---|---|
| 2,298,627 A * | 10/1942 | Proudman et al. ........ | 73/864.63 |
| 3,444,742 A | 5/1969 | Ellis et al. | |
| 3,842,677 A | 10/1974 | Bulkin et al. | |
| 4,470,316 A | 9/1984 | Jiskoot | |
| 4,584,887 A | 4/1986 | Galen | |
| 4,712,434 A * | 12/1987 | Herwig et al. ........... | 73/864.63 |
| 4,800,763 A | 1/1989 | Hakkers et al. | |
| 5,031,469 A * | 7/1991 | Blackburn et al. ....... | 73/864.63 |
| 5,116,330 A * | 5/1992 | Spencer ................... | 73/863.71 |
| 5,131,282 A | 7/1992 | Kuhner | |
| 5,251,495 A * | 10/1993 | Kuhner .................... | 73/863.71 |
| 5,341,692 A * | 8/1994 | Sher et al. ................ | 73/864.63 |
| 5,361,643 A * | 11/1994 | Boyd et al. .............. | 73/863.71 |
| 5,404,763 A | 4/1995 | Guggenheim | |
| 5,566,576 A * | 10/1996 | Sher et al. ................ | 73/864.65 |

(Continued)

FOREIGN PATENT DOCUMENTS

WO    PCT/US01/08652 A1    10/2001

OTHER PUBLICATIONS

U.S. Appl. No. 10/257,514, filed Jul. 1, 2004, Coleman et al.

*Primary Examiner*—Hezron Williams
*Assistant Examiner*—Nashmiya S Fayyaz

(57) ABSTRACT

A gas sampling container (15) capable of obtaining, isolating and transporting samples of gas or other fluid under pressure form. The container (15) further exhibits a plurality of simple, reliable, inexpensive, self sealing, valves (2) which allow introduction, flow through and exit of the gas sample. The container (15) is suitable for taking discrete or serial samples from a gas or fluid flow source and is especially suited for use in automated sampling apparatus. These containers are acceptable for shipment of compressed flammable gases under the regulatory structures of many countries.

10 Claims, 4 Drawing Sheets

U.S. PATENT DOCUMENTS 5,600,075 A * 2/1997 Peterson .................. 73/863.71
2004/0099068 A1 * 5/2004 Welker .................... 73/863.71
2004/0123679 A1 * 7/2004 Coleman et al. ......... 73/863.72

* cited by examiner

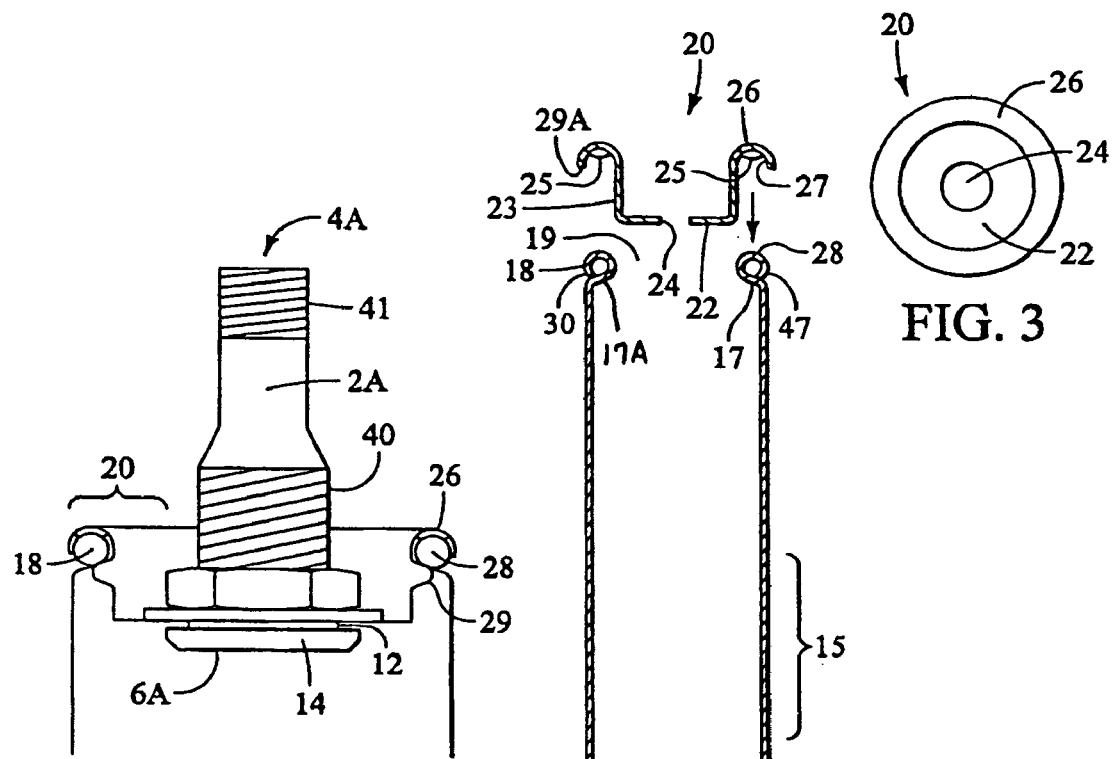
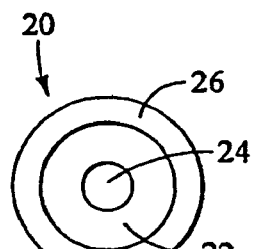
FIG. 3
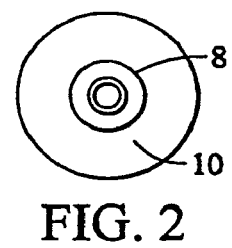
FIG. 2
FIG. 4
FIG. 1

PRESSURIZED GAS SAMPLING CONTAINER

This application is the National Stage of International Application PCT/USO4/38636 filed 12 Nov. 2004 which in turn claimed the benefit of U.S. Provisional Application No. 60/519,410 filed 12 Nov. 2003.

TECHNICAL FIELD

This pressurized gas sampling container relates to the collection, transportation and analysis of gas samples which may be required in various scientific, environmental and resource contexts. As an example, in oil and natural gas exploration, drilling, recovery and storage, periodic sampling of recovered gases and fluid are required for subsequent analysis. In the oil industry, "mud" is a colloquial term for a thick chemical composition that is pumped into drills as they penetrate the substrate. This "mud" is returned to the surface and contains gases that are released from the rock as the drill penetrates. Significant data is acquired from the analysis of these gases.

BACKGROUND ART

International Publication Number WO 01/79805 A1 discloses a non pressurized sampling container in conjunction with a sampling apparatus. This system and non-pressurized sampling container is widely used in the gas sampling industry specifically, in the mud gas sampling sector. U.S. Pat. No. 5,116,330 to Spencer provided for a sample extraction system with a sampling container and valves. Such a sampling system requires the interruption of the fluid flow as sampling containers are exchanged. Further, extraction of the sample from the sampling container was accomplished by "bleeding" the container, a technique which relies on gravity and is suitable for fluids in a liquid rather than a gaseous state. Although less common today, the gas sampling industry utilizes sampling bags which have the obvious problems of fragility, occupying a significant volume when being shipped and the inability to contain gas or fluid under any significant pressure.

DISCLOSURE OF THE INVENTION

This pressurized tube facilitates the recovery and transportation of gas samples. This pressurized sampling container, made from aluminum will be usable at pressures up to 270 pounds per square inch (1860 kPa), however, other materials such as steel or plastic, other polymers, carbon fiber and other metals may allow higher pressures. There are several advantages in utilizing pressurized gas sampling containers. High pressure containers are very expensive and with valves and end caps, can exceed $200.00 per unit. The present invention will retail at approximately $25.00 per unit. More fundamentally, there are currently no readily available low pressure sampling containers on the market with the advantage of flow through gas collection. These types of containers are difficult to purge and thus samples collected in them are generally contaminated with whatever materials were previously in the container.

Further, by compressing the gas, the amount of sample that can be collected is several times larger than with the non-compressed gas sampling containers or tubes. For example, at 150 psi, the amount of sample is actually 11 times as much as a non compressed sample in the same size container. This larger sample size allows additional analyses to be carried out that could not be done on the non-compressed gas sampling containers or tubes. It is anticipated that this container will meet or exceed the United States Department of Transportation requirements for the shipping of compressed gases. Specifically, It is acceptable for shipment of compressed flammable gases under the US Department of Transportation classification UN2037, RECEPTACLES, SMALL, CONTAINING GAS. It is also anticipated the container will meet or exceed similar standards in other countries.

The use of low pressure sampling containers will also simplify shipping. With the currently used non-compressed gas sampling containers or tubes, depending on size, a maximum of 8 per box could be shipped on passenger aircraft and, according to the regulations of the International Air Transport Association (IATA), up to 40 per box could be shipped on cargo-only aircraft. This is a significant disadvantage because many areas of the world do not have cargo-only aircraft service. Because the projects for which the gas sampling containers or tubes are used involve collection of as many as 200 to 300 samples, shipping in small groups is very inefficient and expensive. This has resulted in some samples being sent by ship with a resultant delivery times of several months. For non-compressed gases, shipping quantities are given as volumes (1 liter for passenger aircraft, 5 liters for cargo-only aircraft). For compressed gases, quantity limitations are by net weight. The invention is suitable for the transportation of many kinds of gases, however, consider, for example, using the container to ship natural gas samples. Natural gas is mostly methane and generally lighter than air. Thus, the quantity that can be shipped in one outer package, even on passenger aircraft, is so large that it presents no practical limitation. 25, 50, or even 100 of the compressed gas containers per box will meet regulations.

The ability to ship pressurized samples will also simplify sample collection. Often the lines or apparatus from which gases must be collected is pressurized. An example is the collection of mud gases from oil and gas well drilling operations. In some cases the sample must be drawn from a line that is pressurized to 25 or 30 psi. With the non-compressed gas sampling containers or tubes, it was necessary to reduce the pressure in the container to atmospheric pressure before they could be shipped. This was a complicating factor and resulted in some samples actually being shipped improperly.

The invention has valves on both ends which can be opened and closed independently and which allow the container to be purged by simply flowing the sample gas through it. As long as the quantity of sample gas available is not limiting, the container does not have to be evacuated prior to use. The valves are simple, reliable, self sealing and inexpensive and the invention is readily adaptable for use with automated sample collection and analysis systems.

FIG. 1 is an embodiment of a sample container fashioned from a cylinder having a closed end and a cap disposed over an opened end as opposed to container fashioned from a cylinder having two opened ends. FIG. 1 shows a cross section of a cylinder (15) having a closed end (10), which is perforated by circular cylinder aperture (8). An elevation view of the closed end (10) is seen in FIG. 2, which also exhibits circular aperture (8). Returning to FIG. 1 it is seen that cylinder walls (16) extend toward an open cylinder end (19). The open cylinder end (19) exhibits a rolled lip (18) formed by cylinder wall (16) being formed inward then outward to such an extent that cylinder wall (16) touches itself at point (17) thus forming the rolled lip (18). Cap (20) is shown in FIG. 1 and also in FIG. 3. Cap (20) is cup shaped and of such a diameter that cap sides (19) communicate with rolled lips (18) yet allows cap bottom (22) to slide within cylinder (15) allowing partially rolled flange (26) to also communicate with rolled lip (18). Partially rolled flange is formed in such a way as to allow its inner curved surface (27) to communicate with outer curved surface (28) of rolled lip (18). Seal (25) is annular in shape and rests on the inner curved surface. When cap (20) is fully inserted into cylinder (15), partially rolled flange (26) communicates with seal (25) which, in turn, communicates with rolled lip (18) forming an air or gas tight seal. When partially rolled flange is then further rolled or crimped, the flange end, is pressed under rolled lip (18) at point (30). This tightly compresses seal (25) allowing cylinder (15) to be so tightly sealed as to allow cylinder (15) to contain compressed gasses or liquids. Cylinder (15) will be composed of aluminum, steel or other substance of suitable strength for compressed gasses and liquids. Circular cap aperture (24) is substantially the same diameter as circular cylinder aperture (8). Valve body (2) is inserted through circular cylinder aperture (8) such that valve body first end (4) is exterior to cylinder (15) and valve body second end (6) is interior. Valve body lip (14) causes valve body second end (6) to be retained with cylinder (15) and also allows the compression of seal (12) between valve body lip (14) and cylinder end (10). The valve body is substantially similar to FIG. 5 and it can be seen that valve body (2) is externally threaded. Valve body (2) will accept washer (3) over valve body first end (4) and will also accept internally threaded nut (5) such that when internally threaded nut (5) is threaded over the external threads of valve body (2) it tightens and compresses seal (12) between valve body lip (14) and cylinder end (10) allowing a sufficient seal to retain compressed gasses. A similar valve body is inserted through cap circular aperture (24) with valve body first end (4) exterior to cylinder (15) and valve body second end (6) inside cylinder (15) when cap (20) is inserted into cylinder (15) and resting on rolled lip (28). FIG. 4 illustrates cap (20) inserted through open cylinder end (19) with valve body (2) in proper position through circular cap aperture (24). FIG. 5 also illustrates an alternative crimping method wherein a portion of the cap wall (23) is expanded into lip (29) such that lip (29) applies pressure under rolled lip (18). This, in turn causes partially rolled flange (26) to seat on the upper surface of rolled lip (18) causing seal (25) to be compressed thus sealing the cylinder. Both illustrated crimping methods may be used independently or in conjunction.

BRIEF DESCRIPTION OF THE DRAWINGS

FIG. 1 is a cross sectional view of the sampling container.
FIG. 2 is a plan view of the container closed end.
FIG. 3 is a plan view of the cap.
FIG. 4 is a perspective view of the valve and cap in place within the open end of the sampling container.

BEST MODE FOR CARRYING OUT THE INVENTION

Figure 5:
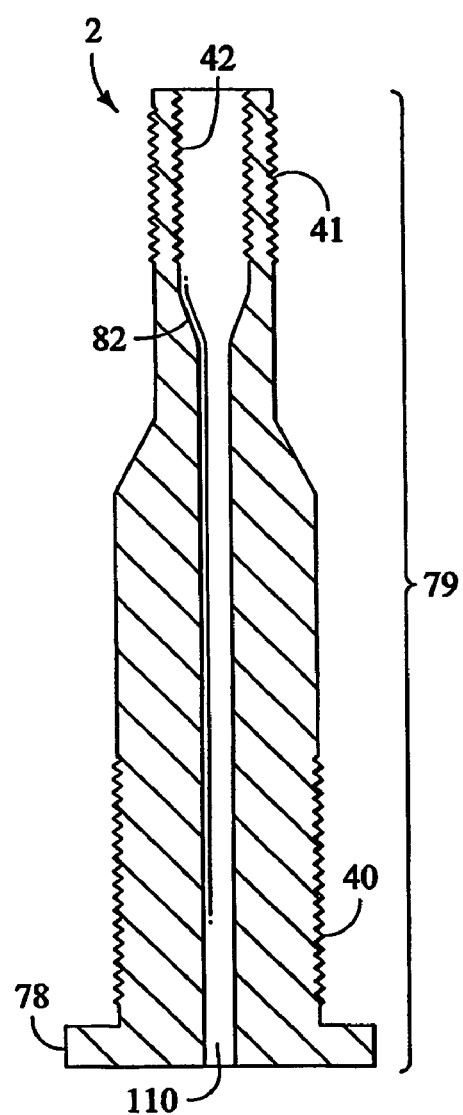
FIG. 5 is a cross section view of the valve body.

FIG. 1 shows a cross section of a container (15) having a closed end (10), which is perforated by circular container aperture (8). An elevation view of closed end (10) is seen in FIG. 2, which also exhibits aperture 8. Turning again to FIG. 1 it is seen that container walls (16) extend toward open container end (19). The open container end (19) exhibits a rolled lip (18) formed by container wall (16) being formed inward toward the longitudinal midline of the container then outward to such an extent that container wall (16) touches itself at point (17) thus forming the rolled lip (18). Cap (20) is shown in FIGS. 1, 3 and 5. Cap (20) is cup shaped and of such a diameter that cap sides (23) communicate with rolled lips (18) yet allows cap bottom (22) to slide within container (15) allowing partially rolled flange (26) to also communicate with rolled lip (18). Partially rolled flange (26) is formed in such a way as to allow inner curved surface (27) to communicate with outer curved surface (28) of rolled lip (18). Seal (25) is annular in shape and rests on the inner curved surface (27). When cap (20) is fully inserted into container (15), partially rolled flange (26) communicates with seal (25) which, in turn, communicates with rolled lip (18) forming an air or gas tight seal. When partially rolled flange (26) is then further rolled or crimped, the flange end (29A), is pressed under rolled lip (18) at point (30). This tightly compresses seal (25) allowing container (15) to be so tightly sealed as to allow container (15) to contain compressed gasses or liquids. Container (15) will be composed of aluminum, steel or other substance of suitable strength for compressed gasses and liquids. Circular cap aperture (24) is substantially the same diameter as circular container aperture (8). First valve (2) is inserted through circular container aperture (8) such that valve first end (4) is exterior to container (15) and valve second end (6) is interior. Valve lip (14) causes valve second end (6) to be retained with container (15) and also allows the compression of seal (12) between valve lip (14) and container end (10). Second valve (2A) is substantially similar to FIG. 5, as is first valve (2) and it can be seen that valve (2A) exhibits external threads, specifically first external thread (40) and second external thread (41). Returning to FIG. 1 it is seen that first valve (2) will accept washer (3) over valve first end (4) and will also accept internally threaded nut (5) such that when internally threaded nut (5) is threaded over the first external thread (40) of valve (2) it tightens and compresses seal (12) between valve lip (14) and container end (10) allowing a sufficient seal to retain compressed gasses. Second valve (2) is inserted through cap aperture (24) with valve first end (4A) exterior to container (15) and valve second end (6A) inside container (15) when cap (20) is inserted into container (15) and resting on rolled lip (28). FIG. 4 illustrates cap (20) inserted through open container end (19) with second valve (2A) in proper position through circular cap aperture (24). FIG. 4 also illustrates an alternative crimping method wherein a portion of the cap wall (23) is expanded into lip (29) such that lip (29) applies pressure under rolled lip (18). This, in turn causes partially rolled flange 26 to seat on the upper surface of rolled lip (18) causing seal (25) to be compressed thus sealing the container. Both illustrated crimping method may be used independently or in conjunction.

Turning now to FIG. 5, the first valve (2) is illustrated. It is composed of a transverse base (78) and annular section (79). Annular section (79), which is attached to the transverse base (78), exhibits external thread (40) and second external thread (41). Central bore (110) extends through both transverse base (78) and the annular section (79). The valve first end (4) exhibits both external threads (41) and internal threads (42) within the central bore (110). The central bore (110) exhibits a conical narrowing, the central bore valve seat section (82). It is here that a plunger-activated valve (85) is seated. Second valve (2A) is configured substantially similar to that of first valve (2).

Figure 6:
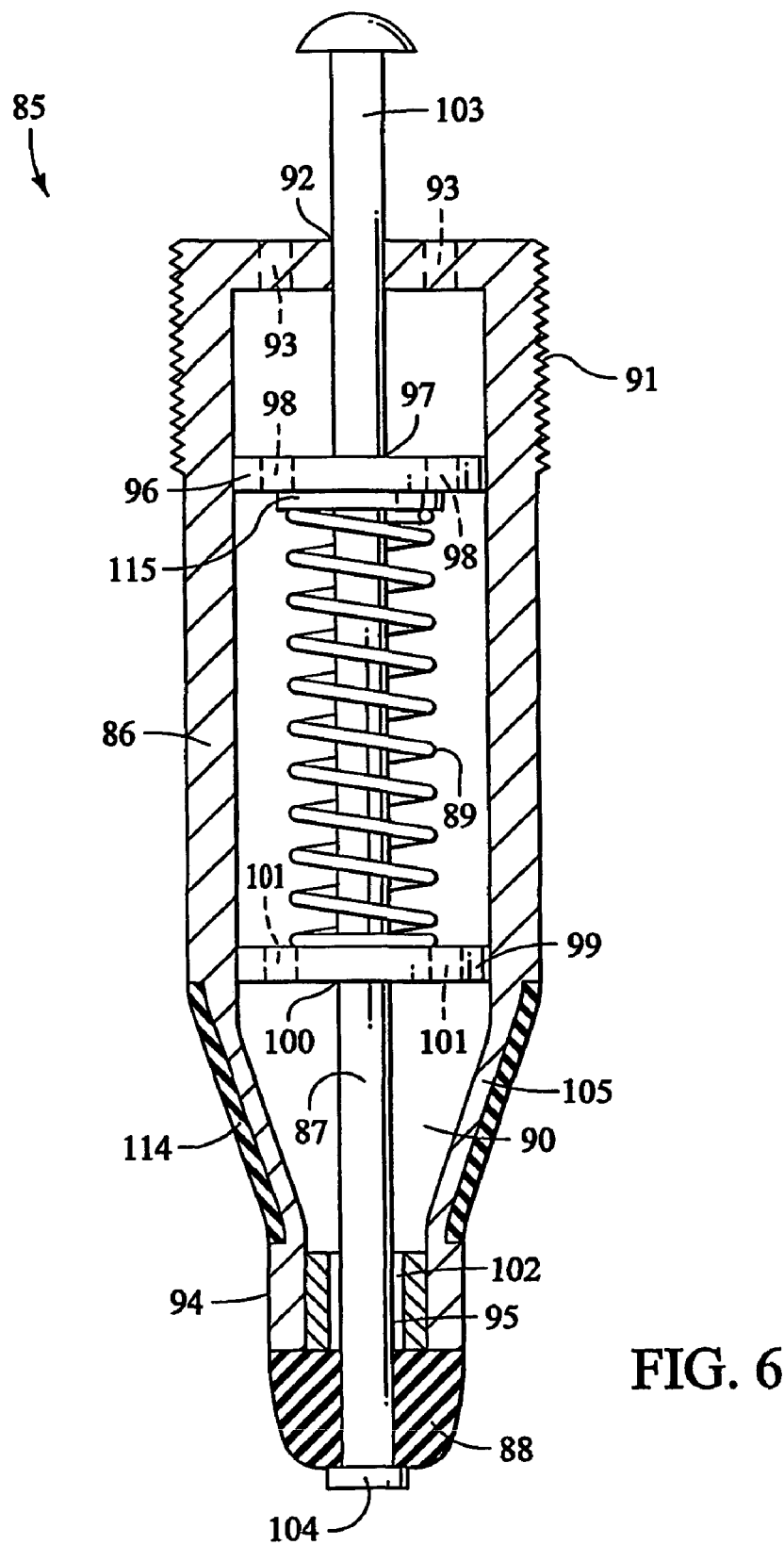
FIG. 6 is a cross section view of the plunger valve.

Turning now to FIG. 6 plunger activated valve (85) is shown. Plunger activated valve 85 is composed of a valve body 86 having a central cavity 90. Externally threaded first plunger valve body end 91 has a central bore 92 and a plurality of apertures 93 that communicate with the central cavity 90. The second plunger valve body end 94 also exhibits a corresponding central bore 95 with an annular space also communicating with the central cavity 90. The exterior of the valve body 86 exhibits a conical plunger valve body segment 105. A plunger valve body gasket 114 is seated around the conical plunger valve body segment 105 and substantially corresponds to the shape of the central bore valve seat section 82 shown in FIG. 5. Within the central cavity 90 area first plunger rod support 96 having a central bore 97 and a plurality of apertures 98. The first plunger rod support is fixed to the interior walls of the central cavity 90. A second plunger rod support 99 also has a central bore 100 and a plurality of apertures 101. The second plunger rod support 99 is also fixed to the interior walls of the central cavity 90. Thus the central bores of the second plunger valve body end 94, the second plunger rod support 99, the first plunger rod support 96 and the first plunger valve body end 91 all correspond such that plunger 87 can be disposed through all. Plunger 87 has a first plunger end 103 disposed outside central cavity 90 and above valve body 86. A second plunger end 104 is also disposed outside the central cavity 90 and below valve body 86. Plunger 87 also exhibits spring stop 115 fixed to plunger 87 between first plunger rod support 96 and second plunger rod support 99 but at a point on plunger 87 where the spring stop 115 communicates with the interior surface of the first plunger rod support 96 when in a resting position. The resting position is maintained by spring 89 disposed over the plunger rod and communicating with spring stop 115 and the second plunger rod support 99. Fixed to the second plunger end 94 in such a manner as to preclude leakage around the plunger 87 is plunger gasket 88. Plunger gasket 88 seals the central bore 95 and annular space 102 of second plunger valve body end 94 by being held against the second plunger valve body end 94 by the pressure exerted by spring 89 on spring stop 115. Now returning to FIG. 5, it can be seen that when second plunger valve body end 94 of plunger activated valve 85 is inserted into first annular section end 80 of first end cap valve body 77, externally threaded first plunger valve body end 91 may be disposed within the internal threads of first annular section end 80. Disposition of plunger activated valve 85 is to such a depth as to press plunger valve body gasket 114 firmly against central bore valve seat section 82 creating a seal.

When first valve 2 and second valve 2A are inserted within their respective apertures, the cap sealed within the sample container, and plunger activated valves are mounted within the valve bodies, the sample container then obtains the ability to seal within it a gas sample. The plunger activated valves, when fluidly connected to an apparatus capable of depressing the plunger valves yet maintaining a seal (such as that seen in International Publication Number WO 01/79805 A1), that is an injection and extraction means, it will result in injection, extraction or flow through of a pressurized gas sample.

Figure 7:
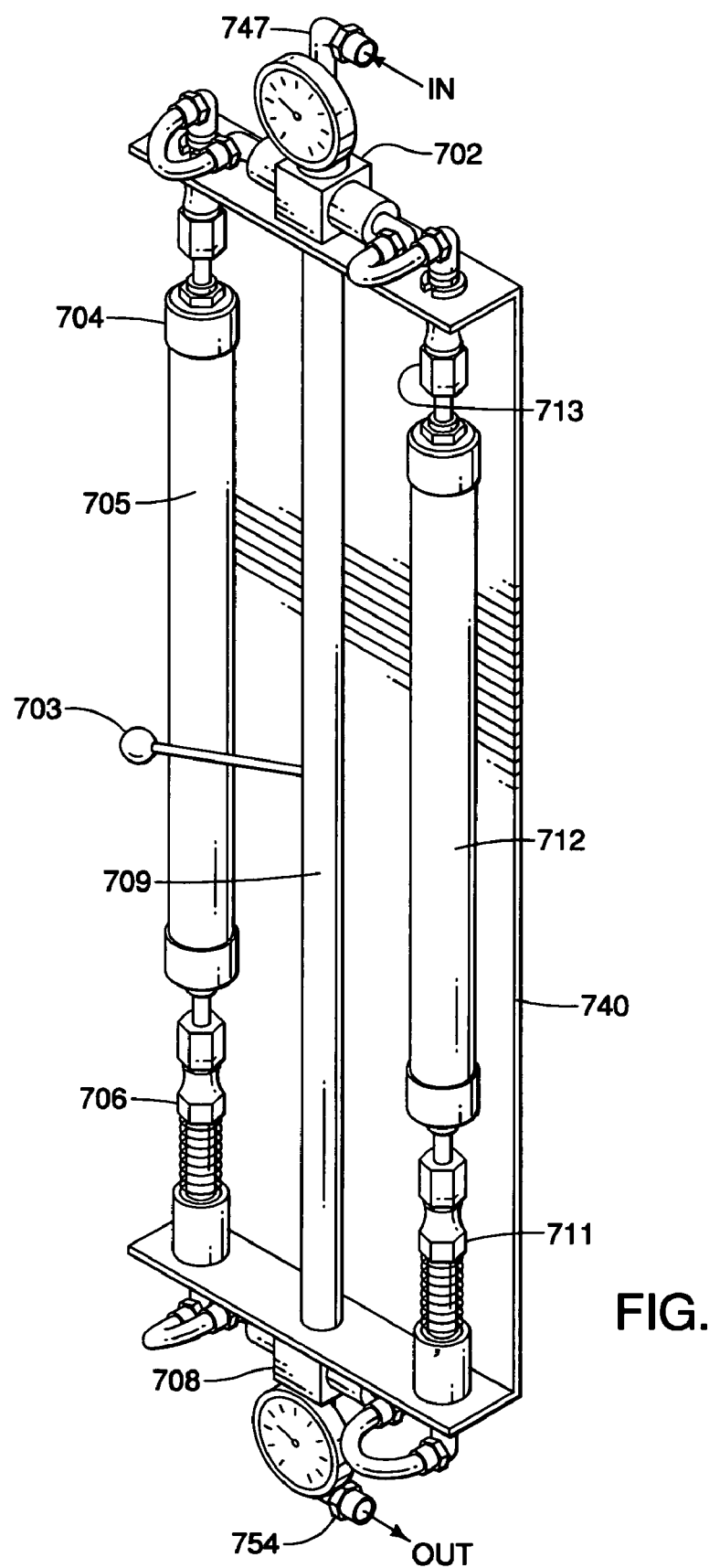
FIG. 7 is a perspective view of the sampling apparatus.

FIG. 7 depicts such an apparatus for taking a sample. Frame 740 supports first 705 and second 712 sample containers between fixed chucks 704 and 713 and spring-loaded chucks 706 and 711, respectively. Material to be sampled is sent to inlet 747, which a connected by a three-way valve 702 to both sample containers via associated as conduits shown in the figure. Another three-way valve 708 leads from both sample containers to a common outlet. Both three-way valves are controlled in tandem by handle 703, connected to a shaft 709, connecting the both three-way valves together, so that inlet flow is sent to a particular sample container supported in the frame; the intermediate position of the handle closes the two outlets for both valves.

INDUSTRIAL APPLICABILITY

This pressurized gas sampling container finds application in the oil and gas industry and any industry or application in which the discrete or continuous sampling of gases or fluids are required in which a pressurized sample is desired which needs to be economically an efficiently transported to a location where the sample is removed for testing.

What is claimed is:

1. A sampling container, comprising:
   a body;
   a closed body end perforated by an aperture having a first self-sealing valve disposed thereacross;
   an open body end; and
   a cap having cap aperture and a second self-sealing valve disposed thereacross, said cap disposed within said open body end and attached thereto in a gas tight seal;
   said first and second self-sealing valves each comprises a spring-loaded plunger slidably disposed therein and biasing an end of the plunger against a gasket in a normally closed position;
   said container adapted for being mounted for fluid collection in a sampling apparatus, said self-sealing valves being normally closed and being opened by mounting said container in such apparatus;
   wherein the sampling apparatus comprises
   a plurality of chucks into which said first and said second self-sealing valve may be disposed creating a gas tight seal, said plurality of chucks capable of opening said first and second self-sealing valves.

2. The container of claim 1 wherein said open body end is defined by a rolled lip.

3. The container of claim 2 wherein said cap comprises a partially rolled flange and said flange is pressed under said lip to seal the cap to the body.

4. The sampling container of claim 2 wherein said cap comprises a partially rolled flange and said flange is crimped onto said lip.

5. The sampling container of claim 2 wherein said cap comprises (a) a partially rolled flange and (b) a wall having an expanded lip formed therein, said wall extending into said open end, whereby said cap is sealed to said body by compression of said rolled lip between said partially rolled flange and said expanded lip.

6. The sampling container of claim 1 wherein said first and second self-sealing valves disposed coaxially in said container, and each valve having a slidable plunger biased in a normally closed position.

7. The sampling container of claim 1 wherein said first and second self-sealing valves are opened independently.

8. The sampling container of claim 1 wherein said body is a material selected from the group consisting of metals, polymers, and carbon fiber.

9. The sampling container of claim 8 wherein said body comprises steel or aluminum.

10. The sampling container of claim 1 housing a pressurized sample.

* * * * *